United States Patent [19]

Laenger et al.

[11] Patent Number: 4,809,696

[45] Date of Patent: Mar. 7, 1989

[54] FUNCTIONAL ELECTRICAL STIMULATION SYNCHRONIZER SWITCH

[75] Inventors: Charles J. Laenger; Henry L. Hughes; Thomas C. Burk, all of Tulsa, Okla.

[73] Assignee: Hillcrest Medical Center, Tulsa, Okla.

[21] Appl. No.: 99,092

[22] Filed: Sep. 21, 1987

[51] Int. Cl.[4] ............................................. A61N 1/36
[52] U.S. Cl. ............................................. 128/419 R
[58] Field of Search ........... 128/419 R, 420 R, 420 A, 128/421, 423, 423 W; 272/73

[56] References Cited

U.S. PATENT DOCUMENTS

| | | | |
|---|---|---|---|
| 4,389,627 | 6/1983 | Uesugi et al. | 335/206 |
| 4,421,336 | 12/1983 | Petrofsky et al. | 128/421 |
| 4,480,830 | 11/1984 | Petrofsky et al. | 128/423 W |
| 4,499,900 | 2/1985 | Petrosfky et al. | 128/423 W |
| 4,556,214 | 12/1985 | Petrosfky et al. | 128/423 W |
| 4,570,927 | 2/1986 | Petrofsky et al. | 272/73 |
| 4,586,510 | 5/1986 | Glaser et al. | 128/423 W |
| 4,642,769 | 2/1987 | Petrofsky . | |

FOREIGN PATENT DOCUMENTS

| | | | |
|---|---|---|---|
| 283602 | 10/1912 | Fed. Rep. of Germany ... | 128/420 A |
| 2222844 | 11/1973 | Fed. Rep. of Germany ...... | 128/420 |
| 858849 | 9/1981 | U.S.S.R. .......................... | 128/419 R |

Primary Examiner—Lee S. Cohen
Attorney, Agent, or Firm—Head & Johnson

[57] ABSTRACT

This is an electrical stimulating device which is used with an exerciser having bicycle-like pedals to aid people with paralyzed legs. Several miniature magnetic reed switches are mounted in a first and a second semi-circular arrays on a switchboard. The switchboard is placed in a plane parallel to the plane on which the pedals rotate. The pedal carries a permanent magnet which rotates in a plane adjacent to the switches and sequentially activates the reed switches. The activation of the reed switches directs the stimulation pulses from a neuromuscular simulator (NMS) to the patient's quadriceps to effect total extension of the leg.

5 Claims, 5 Drawing Sheets

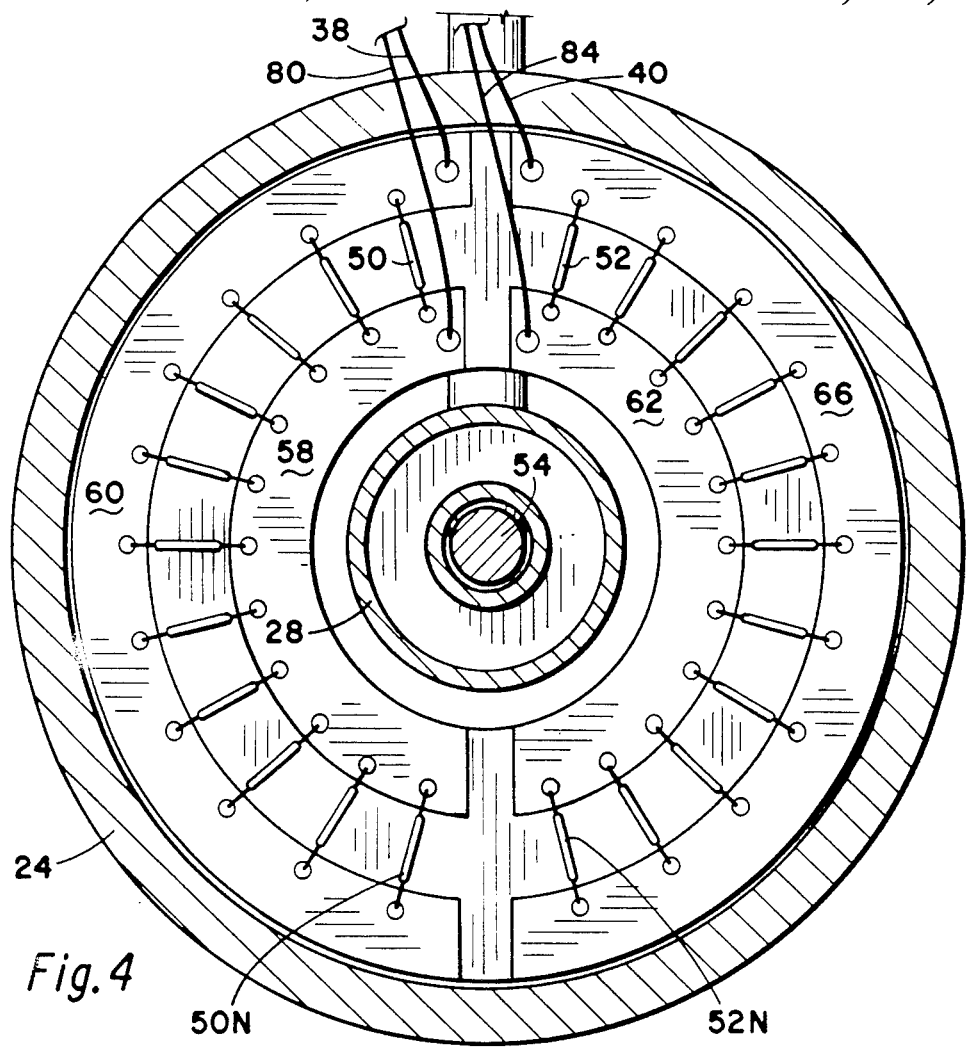
Fig. 4
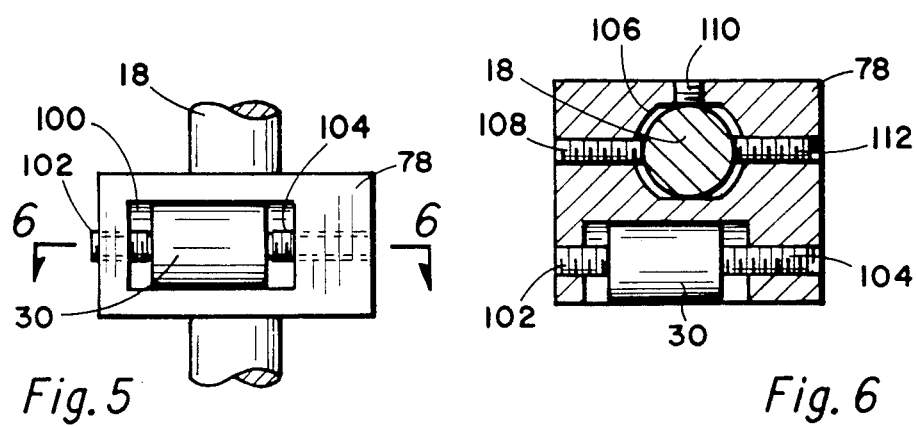
Fig. 5
Fig. 6

FUNCTIONAL ELECTRICAL STIMULATION SYNCHRONIZER SWITCH

DISCLOSURE STATEMENT

A preliminary patentability search revealed the following patents:
U.S. Pat. No. 4,389,627, Uesugi et al
U.S. Pat. No. 4,436,097, Cunningham
U.S. Pat. No. 4,480,830, Petrofsky et al
U.S. Pat. No. 4,499,900, Petrofsky et al
U.S. Pat. No. 4,570,927, Petrofsky et al
U.S. Pat. No. 4,520,827, Wright et al
U.S. Pat. No. 4,586,495, Petrofsky No reference was found disclosing the stimulation synchronizing switch described herein. U.S. Pat. No. 4,389,627, Uesugi et al shows a changeover switch comprising a plurality of magnetic reed switches disposed in a circular array, but no suggestion is made about a stimulation device. The other listed patents disclose exercising devices including bicycles in combination with stimulation means for stimulating the patient's legs. U.S. Pat. No. 4,499,900, Petrofsky et al includes a position sensor which senses the position of the pedals and transmits indication thereof to a computer which generates control signals for stimulating driving circuits connected to a stimulation electrode.

BACKGROUND OF THE INVENTION

The present invention relates to applying electrical pulses to muscles that have been at least partially paralyzed.

Far too many injuries to people resulting in spinal damage occur each year. This type damage can often produce partial or total paralysis of muscles which are controlled from a point below the point of spinal cord damage. The victim then faces a life of relative inactivity and deterioration of muscles which otherwise would be active. Various physical therapy methods have been developed in recent years to assist in maintaining muscle integrity in such positions. One of these methods involves the use of electrical pulses. It is known that treating disease with electricity has intrigued man for centuries. However, recently there has been developed more sophisticated electrical stimulation programs. It has been found that in the presence of intact peripheral nerve excitability, an external source of excitation can induce functional motor responses for many patients who demonstrate difficulties in voluntary movement. Information on this has been reported in Functional Electrical Stimulation-A Practical Clinical Guide-Second Edition, developed at the Rancho Los Amigos Rehabilitation Engineering Center in Downey, Calif. That report states that common candidates for neuromuscular electrical stimulation includes the patient recovering from a cortical neuron lesion such as caused by stroke or head trauma; the spinal injury patient; the orthopedic surgical patient and some patients recovering from lower motor neuron disorders.

There have been several rotary apparatus for stimulating muscles to aid in the rehabilitation or exercise of the muscles involved. However, those of which we are aware are rather expensive ranging from $18,000–$40,000 or more. This precludes many people from having one of these in their homes.

It is therefore an object of this invention to disclose an apparatus that is simple and relatively inexpensive, but still very effective.

SUMMARY OF THE INVENTION

We have developed means for applying electrical signals to produce impulses to be applied to the leg muscles of paralyzed individuals to enable that person to pedal an exerciser having bicycle-like pedals and pedal arms. We use miniature magnetic reed switches which are mounted on a circuit board in slightly less than semi-circular arrays. The arrays are in a plane parallel to that described by motion of the pedal arm. A permanent magnet is attached to the pedal arm and as the arm is turned the magnet sequentially activates each switch as it passes by it. Thus the synchrony provided is independent of rotary velocity. As each miniature switch is closed, electrical impulses developed in a free-running pulse generator are delivered to the muscle being treated.

It is imperative that the pedal arms be about 15° or so past "top-dead-center" when pressure is applied to the pedal. It is also essential that pressure be removed when the pedal is about 15° or so above bottom dead center. The results are essentially that the other pedal be similarly synchronized. The magnetic reed switches are positioned to obtain this.

The magnetic reed switches are placed in array which occupies slightly less than a semi-circle. Where the magnetic reeds are omitted from the semi-circle they define a first window which is an arc plus or minus fifteen degrees from position zero degree and a second window which is an arc plus or minus fifteen degrees from position 180° to assure onset of stimulation and removal of stimulation at fifteen degrees past "top-dead-center" and "bottom-dead-center" respectively. There will thus be stimulating pulses applied to the muscle during the time the magnet on the pedal rotates from the first magnetic reed switch to the last switch in each array. During the time that the magnet passes over the first array of switches one leg will be stimulated to drive the pedal forward. When that pedal reaches the down position that leg will no longer receive stimulation pulses and the muscles will be relaxed. The momentum of the pedal will carry the other pedal beyond the top-dead-center so that the magnet will approach the first magnetic reed switch in the second array so that the muscle in the other leg will be stimulated in a like manner as was the muscle in the first leg. This operation of course continues as long as the patient desires to exercise the muscles of the legs.

BRIEF DESCRIPTION OF THE DRAWINGS

FIG. 4 is a view taken along the line 4—4 of FIG. 3.

FIG. 5 is a view taken along the line 5—5 of FIG. 3.

FIG. 6 is a view taken along the line 6—6 of FIG. 5.

DETAILED DESCRIPTION OF THE INVENTION

Figure 1:
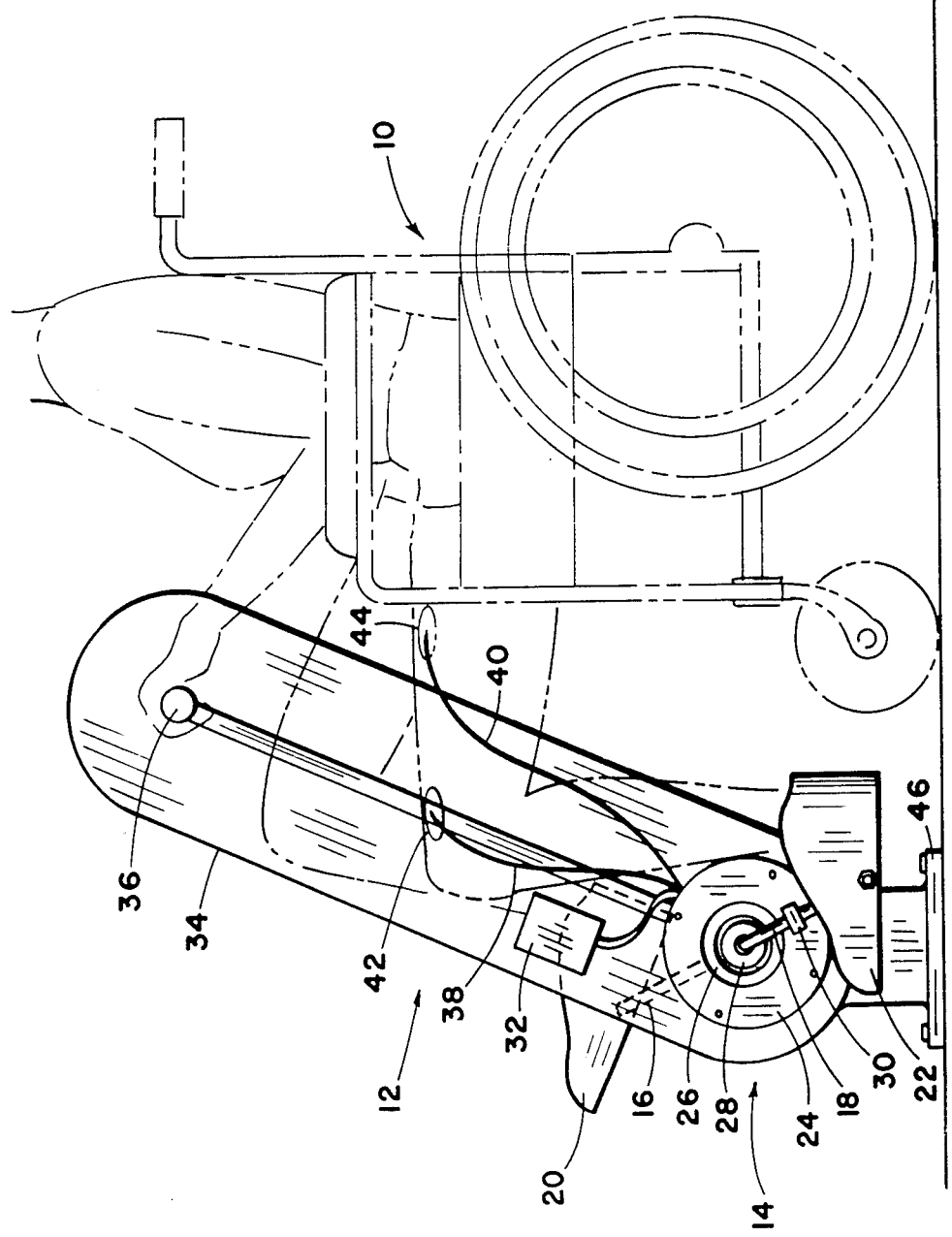
FIG. 1 shows our bicycle-like muscle stimulation exerciser being used by a person in a wheelchair.

Attention is first directed to FIG. 1 which shows a patient in a wheelchair 10 which is in operating position against the exerciser 12 which has a bicycle-like pedal system 14. This pedal system 14 includes a first arm 16, a second arm 18 and boots or foot stirrups 20 and 22 connected to the arms, respectively. The pedal assembly of this invention includes a cover plate 24 a switchboard 26 and bearing housing 28 through which the axle of arms 16 and 18 extend. A permanent magnet 30 is mounted on arm 18. A stimulator or electric pulse source 32 is provided on the housing 34 of the exerciser. Source 32 is of a type to generate the electrical pulses of the repetition rate, width and amplitude for stimulating selected muscles of the patient. These stimulators are commercially available. A handle 36 is provided at the top of the housing 34 for grasping by the hands of the patient. As will be explained more fully in regard to other figures in the drawings herein, the output of source stimulator 32 is fed through electrical leads 38 and 40 to electrodes 42 and 44, respectively, which are shown on the left leg of the patient. Similar electrodes and leads may be placed on the right leg. Although these electrodes are shown as being placed on the quadricep muscles they could be upon any muscles which it is desired to stimulate. One of the electrodes such as 42 is positive and the other electrode 44 is negative. This permits current flow between positive and negative electrodes. The excitation of muscles by electricity has been well documented in the aforesaid Functional Electrical Stimulation publication. The exerciser housing 12 is supported from foundation 46 which may be bolted to the floor or to a sufficiently large foundation to hold it.

Figure 2:
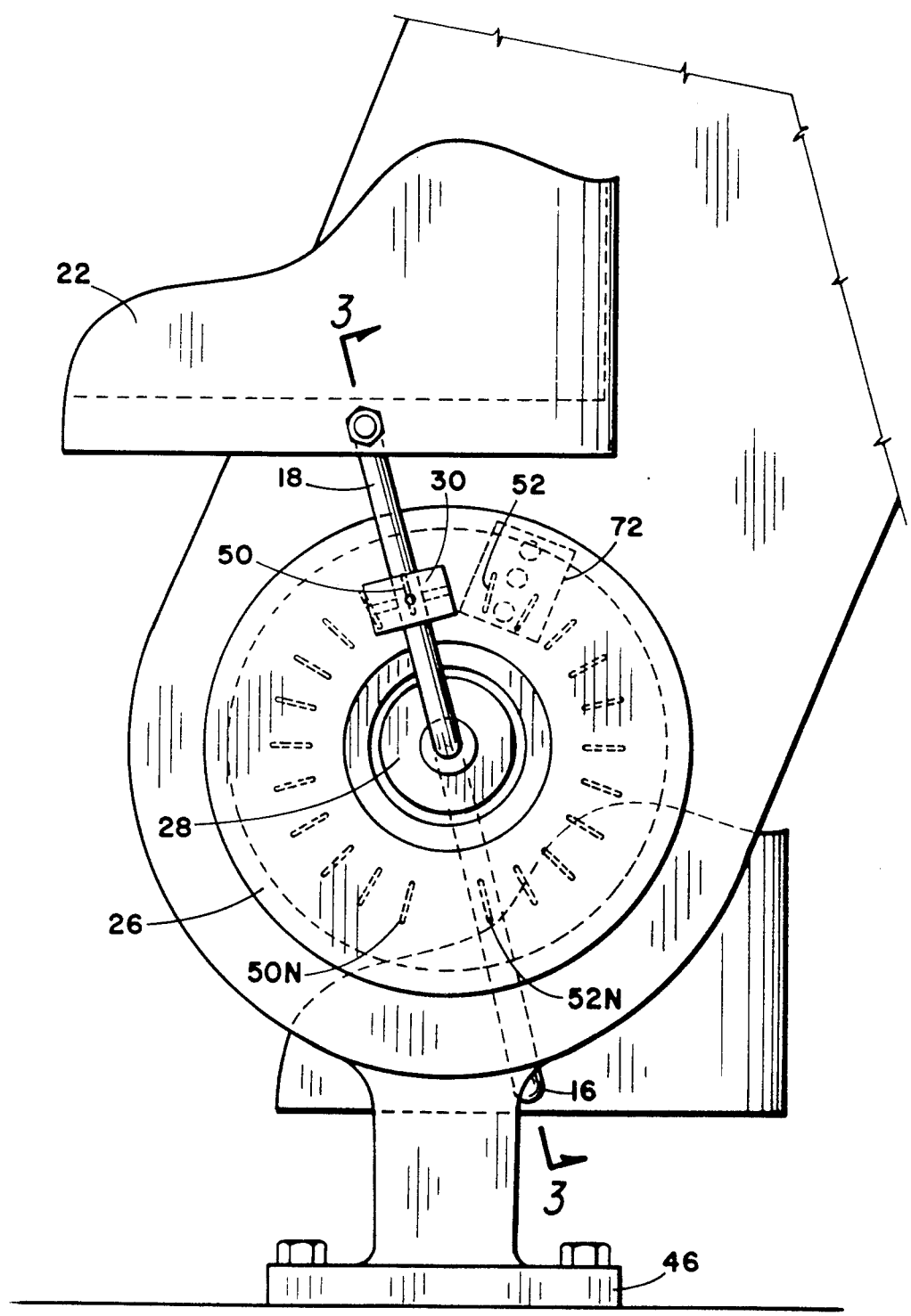
FIG. 2 is an enlarged view of the pedal arrangement of the apparatus of FIG. 1.

Attention is next directed to FIG. 2 which shows an enlarged view of the pedal arrangement. Shown on switch board 26 are two arrays of miniature magnetic reed switches. The first array includes magnetic switches 50 to 50N and the second array includes switches 52 to 52N. Each array is in an arc which is slightly less than a semi-circle. Individual switches in each array are typically about 7.5° apart, center to center. Switches 50N and 52N are preferably approximately thirty degrees apart and switches 50 and 52 are preferably approximately thirty degrees apart. Thus the first array of switches 50 to 50N occupies an arc of a circle of about one hundred fifty degrees. Likewise the arc defined by switches 52 to 52N define an arc of a circle of about one hundred fifty degrees. The reason for this separation of the two arrays of switches is that the pedal arms should be about fifteen degrees past "top-dead-center" when pressure is applied to the pedal. It is also important that pressure be removed from the pedal at about fifteen degrees above "bottom-dead-center". It is also desirable that the alternate pedal be similarly synchronized. These conditions apply to pedaling a bicycle whether or not the rider is disabled. It is noted that racing enthusiasts apply force in both the downstroke and upstroke while a casual rider ordinarily does not.

The permanent bar magnet 30 is so positioned on arm 18 that its motion describes a circle whose radius is approximately the same as the radius of the center of the magnetic reed switches. In one installation the magnetic reed switches were placed so that the center of the magnetic reeds were on a radius of 1.65 inch. That is, the reed switches were placed in holes spaced apart such that they have a radii of 1.3 inches and 2.0 inches. This would make the radius of the middle position between these two holes 1.65 inches. The permanent bar magnet 30 is positioned on arm 18 so that its motion describes a circle whose radius is about 1.65 inches. When an arm 18 is in the uppermost position it should be approximately halfway between micro reed switches 50 and 52 and when in the down position it should be approximately between reed switches 50N and 52N.

Figure 3:
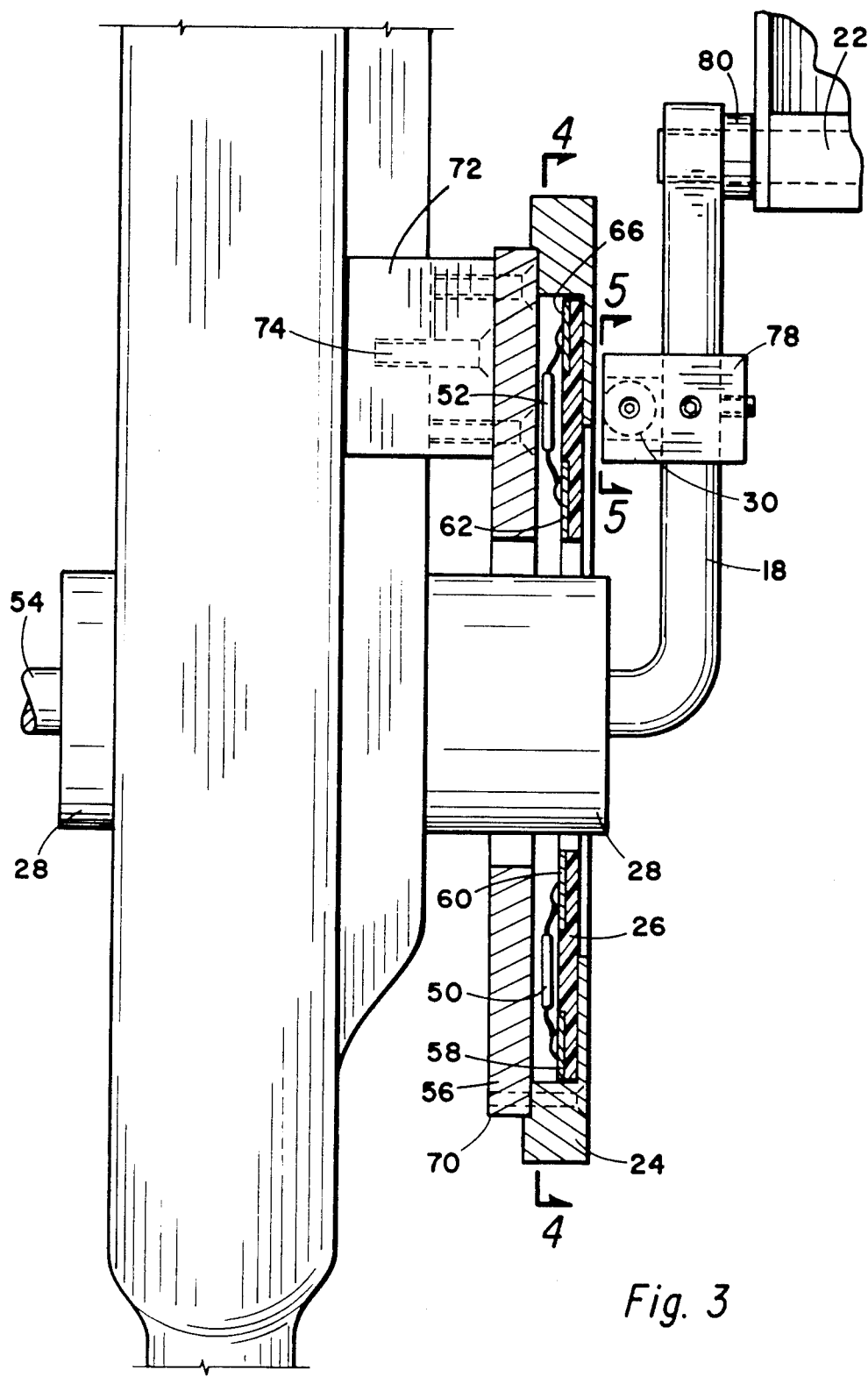
FIG. 3 is a view taken along the line 3—3 of FIG. 2.

Attention is next directed to FIG. 3 which shows a view along the line 3—3 of FIG. 2 and shows the arrangement of switching board and its complementary parts in more detail. Shown thereon is arm 18 with axle 54 extending through bearing housing 28 to be connected with the other arm 16. Shown thereon is a switchboard plate 26 upon which the first array having reeds 50 to 50N are mounted. One end of the switch is connected to an arcuate electrical conductive contact section 60 and the other end of the reed switch 50 is connected to an electrical arcuate conductive contact section 58. These contact sections 58 and 60 extends approximately the same degrees as the array of switches 50 to 50N. The switchboard plate 26 is preferably made of a nonconductive material. The other array of switches is likewise provided with contact arcuate sections mounted on switchboard plate 26. The other array includes the magnetic switches 52 to 52N which are connected at one end to electrical conduction arcuate contact section 62 and the other one at arcuate conductive contact section 66. These contacts are supported by the switchboard plate 26. Contacts 62 and 60 are quite similar to contacts 58 and 60 and serve the same function. The switchboard plate 26 is held in position by a cover plate 24 attached to mounting plate 56 such as by screws 70. The mounting plate 70 is held to the frame by channel adapter member 72 which is attached to the frame by bolts 74 and to the mounting plate 56 by bolts 76. As also can be seen in FIG. 3 magnet 30 is supported in housing 78 which is selectively positioned along arm 18 so that the magnet is positioned about the center point of magnetic reed switch 52 as explained above. A spacer 80 is used to hold the stirrup 22 the desired distance from the arm 18. Attention is next directed to FIG. 5 which shows magnet 30 mounted within housing 78 and can be positioned in cavity 100 by setting of set screws 102 and 104 to obtain the desired position therein. As shown in FIG. 6 arm 18 is positioned in cavity 106 of housing 78. Cavity 106 is made large enough to go over the top of arm 18. The arm 18 has a three-way adjustment which includes screws 108, 110 and 112. This helps obtain the proper alignment of the magnet 30.

Figure 7:
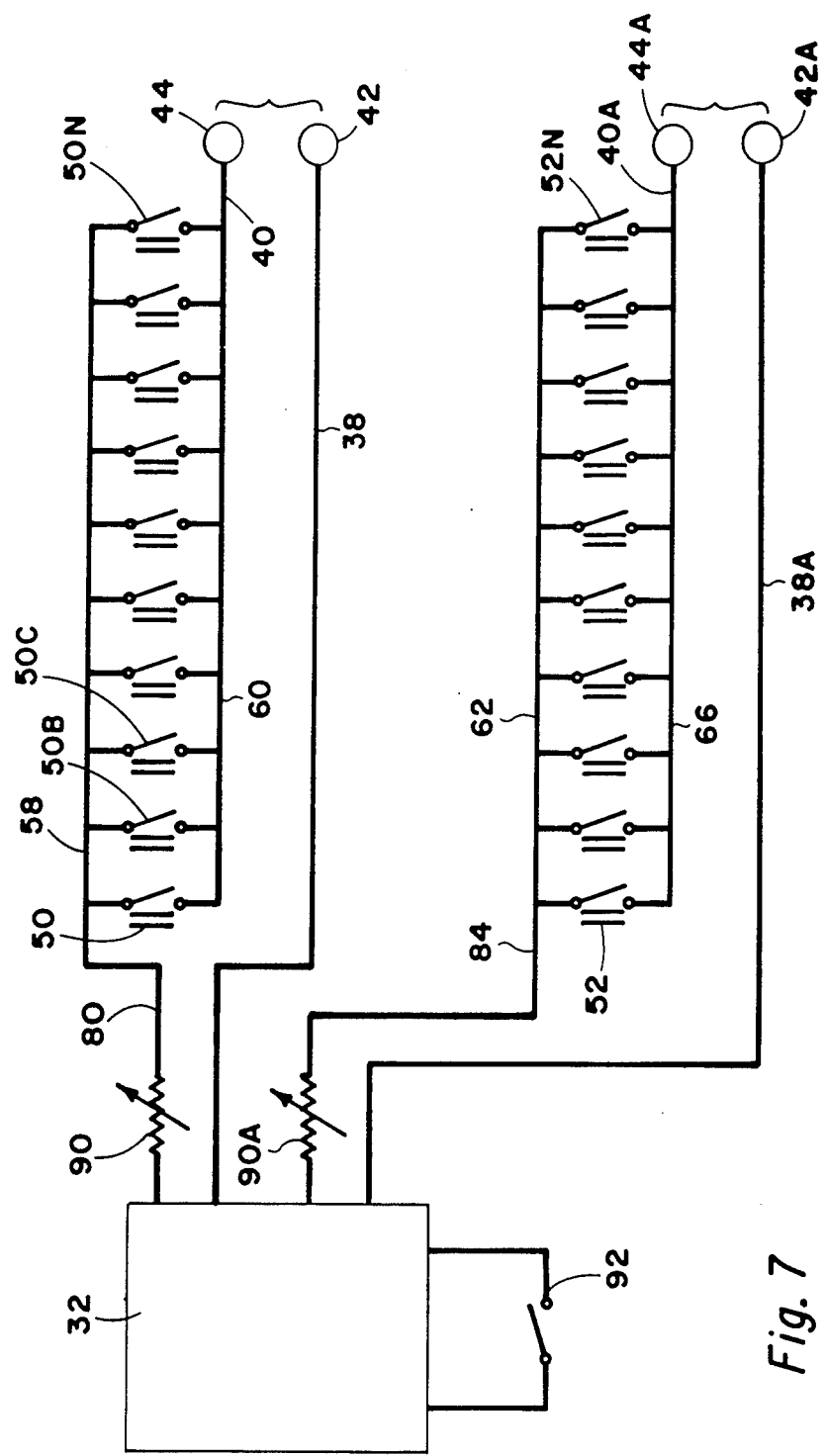
FIG. 7 is a schematic view of the switching circuit.

Attention is next directed to FIG. 4 which shows a view along the line 4—4 of FIG. 3. Here the various reed switches are more clearly shown. As shown, reed switches 50 to 50N are connected at one end to arcuate contact section 58 and the other end to arcuate contact section 60. The electrical leads 80 and 38 are respectively connected to arcuate contacts 58 and 60. Likewise, arcuate contact section 62 and exterior arcuate contact 66 are connected respectively to electrical leads 84 and 40. There are thus shown two arrays of switches. The first array includes the arcuate contacts 58 and 60 and reed switches 50 to 50N. When any one of these reed switches is closed that completes the circuit through electrical conductors 80 and 38. Likewise, the second array includes the inner arcuate contact 62 and the outer arcuate contact 66 which are connected by magnetic reed switches 52 to 52N. Anytime any switch 52 to 52N is closed, which it will be by the passing of the magnet 30, the circuit is completed between conduits 84 and 38A. This is schematically illustrated in FIG. 7. There is shown a muscle stimulation pulse source 32 which is energized by master switch 92. The upper set of magnetic reed switches 50 to 50N can be considered the first array and the lower switches 52 to 52N can be considered the second array. The first array is a part of a circuit involving an output from stimulator source 32 to electrodes 44 and 42 which would be placed on the muscles which are to be exercised. The placement of the electrodes 44 and 42 are at the proper distance at the proper position to obtain the desired results. These electrodes will be activated to input an electrical pulse train into the muscle whenever the circuit is closed. This occurs whenever the magnet closes one of the switches 50 to 50N. The source 32 is energized by closing the switch 92 and has an output between leads 80 and 38 but it passes through the electrodes 44 and 42 only when the circuit is completed as by closing one of the switches 50 to 50N. A variable resistor 90 is included in conduit 80 so that the magnitude of the pulses can be controlled. The second array is identical to the first array and includes conduits 84 and 38A coming from the pulse source 32. Conduit 38A from the source 32 and electrical conduit 40A from the second array of switches are connected respectively to electrodes 42A and 44A. This operation would be the same as that of the first array.

In operation, we assume that the patient is one whose legs are paralyzed. The patient is then placed in wheelchair 10 and is maneuvered to the position shown in FIG. 1. At this time the patient's feet are placed in the stirrups or boots and is ready to begin the exercise. Source 32 is then activated. When the pedals are at top-dead-center and bottom-dead-center none of the magnetic reed switches are activated and no stimulation or muscle contraction, consequently no force occurs on the pedal. When the pedals and pedal arms are rotated to a point fifteen degrees past top-dead-center by an assistant, or with the arms of the patient, the first magnetic reed switch 50 is closed and electrical stimulation is applied to that leg through electrodes 42 and 44. As the pedal arm rotates, the magnet passes from switch 50 to 50B and switch 50 opens and 50B comes under the influence of the magnetic field provided by the bar magnet 30 and that second switch closes. This action and muscle stimulation continues until the pedal arm reaches a point about fifteen degrees above bottom-dead-center. Then all the magnetic switches are open and electrical stimulation of that muscle is removed. The muscle is relaxed and a portion of that force is removed. Inertia drives the other pedal past top-dead-center and a similar sequence of events occurs with the second array of switches for the other leg.

The switching system described herein inherently provides accurate timing and is independent of pedal rotational velocity. That is, the onset of stimulation always begins at fifteen degrees pedal past top-dead-center and closes fifteen degrees below or before bottom-dead-center. This system is simple and inexpensive. The variable resistors 90 and 90A can be used to increase or decrease the electrical stimulation.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. An apparatus for stimulating the muscles of a rider of a stationary exerciser, said rider having a left leg and a right leg which comprises:
    a first arm and a second arm, each arm having a pedal so that the rider's left foot may be placed on one pedal and the right foot on another pedal;
    a source of electrical impulses;
    a flat switch plate having a first and a second array of individual switches operable by magnetic field, said switches being arranged in a circular pattern into a first and second array, the said first array being positioned in a first semi-circle of said circle and the second array being positioned in the second semi-circle thereof;
    at least two stimulating electrodes for application to the muscles of the legs of said rider, one electrode connected to one of said arrays and another electrode connected to the other of said arrays;
    a permanent magnet attached to one arm of one of said pedals so that motion of the arm describes a plane adjacent the switch plate so that rotation of the arm moves the magnet in a circle adjacent said first and second arrays so that the individual switches are sequentially activated by the magnet;
    first means connecting said first array to said source;
    second means connecting said second array to said source.

2. An apparatus as defined in claim 1 in which the two arrays are about thirty degrees apart at each end and the individual switches of each array are about 7.5° apart.

3. An apparatus for stimulating the muscles of a rider which comprises:
    an exerciser having pedals with arms said pedals capable of being set into motion;
    a source of electrical impulses for applications to the muscles of said rider;
    a first array of magnetic switches which is arranged in an arc of a circle and being less than 180°, said array being in a plane parallel to the motion of said pedals;
    a second array of magnetic switches in a second arc of said circle, said second arc being less than 180°;
    an actuating magnet attached to one of the arms of one of said pedals such that the motion of the pedal carries the magnet along said first and second array to sequentially activate the individual magnetic switches therein;
    first means connecting said first array to said source;
    second means connecting said second array to said source;
    a first and a second stimulating electrode for applying impulses to the muscles of said rider;
    third and fourth connecting means connecting said first and second stimulating electrode to first array and said second array, respectively.

4. An apparatus as defined in claim 3 in which the arc of said first array is about one hundred fifty degrees with a thirty degree space void of switches and the center of said void may be called a top-dead-center position and said portion is disposed with respect to the pedals such that when one of the pedals is in an uppermost position, no switch of said first array is activated for fifteen degrees of rotation.

5. An apparatus as defined in claim 4 in which the magnet is positioned so that as the magnet is rotated it is at the center of the magnetic switches.

* * * * *